(12) United States Patent
Wasicek (10) Patent No.: US 8,038,696 B2
(45) Date of Patent: Oct. 18, 2011

(54) SHEATH FOR USE WITH AN EMBOLIC PROTECTION FILTER

(75) Inventor: Lawrence D. Wasicek, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1267 days.

(21) Appl. No.: 11/005,934

(22) Filed: Dec. 6, 2004

(65) Prior Publication Data

US 2006/0122643 A1 Jun. 8, 2006

(51) Int. Cl.
*A61M 29/00* (2006.01)
(52) U.S. Cl. .................................................. 606/200
(58) Field of Classification Search ............... 606/200; 623/1.13, 1.23, 1.35
See application file for complete search history.

(56) References Cited

U.S. PATENT DOCUMENTS

| | | |
|---|---|---|
| 3,472,230 A | 10/1969 | Fogarty |
| 3,592,186 A | 7/1971 | Oster |
| 3,683,904 A | 8/1972 | Forster |
| 3,889,657 A | 6/1975 | Baumgarten |
| 3,952,747 A | 4/1976 | Kimmell, Jr. |
| 3,996,938 A | 12/1976 | Clark, III |
| 4,046,150 A | 9/1977 | Schwartz et al. |
| 4,425,908 A | 1/1984 | Simon |
| 4,447,227 A | 5/1984 | Kotsanis |
| 4,580,568 A | 4/1986 | Gianturco |
| 4,590,938 A | 5/1986 | Segura et al. |
| 4,619,246 A | 10/1986 | Molgaard-Nielsen et al. |
| 4,631,052 A | 12/1986 | Kensey |
| 4,643,184 A | 2/1987 | Mobin-Uddin |
| 4,650,466 A | 3/1987 | Luther |
| 4,662,885 A | 5/1987 | DiPisa, Jr. |
| 4,705,517 A | 11/1987 | DiPisa, Jr. |
| 4,706,671 A | 11/1987 | Weinrib |
| 4,723,549 A | 2/1988 | Wholey et al. |
| 4,728,319 A | 3/1988 | Masch |
| 4,733,665 A | 3/1988 | Palmaz |
| 4,790,812 A | 12/1988 | Hawkins, Jr. et al. |
| 4,790,813 A | 12/1988 | Kensey |
| 4,794,928 A | 1/1989 | Kletschka |
| 4,794,931 A | 1/1989 | Yock |
| 4,800,882 A | 1/1989 | Gianturco |

(Continued)

FOREIGN PATENT DOCUMENTS

DE  28 21 048  7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner* — Gary Jackson
*Assistant Examiner* — Erin Colello
(74) *Attorney, Agent, or Firm* — Seager, Tufte & Wickhem, LLC (57) ABSTRACT

An embolic protection filtering device and methods and making and using filtering devices. An example filtering device may include an elongate shaft or filter wire, a filter coupled to the filter wire, and a sheath. The methods for using the filtering device include using an introducer member to help back load a guidewire into the sheath and then advance the filtering device along the guidewire to a target region.

22 Claims, 11 Drawing Sheets

U.S. PATENT DOCUMENTS

| | | | |
|---|---|---|---|
| 4,807,626 A | 2/1989 | McGirr | |
| 4,842,579 A | 6/1989 | Shiber | |
| 4,857,045 A | 8/1989 | Rydell | |
| 4,857,046 A | 8/1989 | Stevens et al. | |
| 4,867,157 A | 9/1989 | McGurk-Burleson et al. | |
| 4,873,978 A | 10/1989 | Ginsburg | |
| 4,886,061 A | 12/1989 | Fischelle et al. | |
| 4,898,575 A | 2/1990 | Fischell et al. | |
| 4,907,336 A | 3/1990 | Gianturco | |
| 4,921,478 A | 5/1990 | Solano et al. | |
| 4,921,484 A | 5/1990 | Hillstead | |
| 4,926,858 A | 5/1990 | Gifford, III et al. | |
| 4,950,277 A | 8/1990 | Farr | |
| 4,955,895 A | 9/1990 | Sugiyama et al. | |
| 4,957,482 A | 9/1990 | Shiber | |
| 4,969,891 A | 11/1990 | Gewertz | |
| 4,979,951 A | 12/1990 | Simpson | |
| 4,986,807 A | 1/1991 | Farr | |
| 4,998,539 A | 3/1991 | Delsanti | |
| 5,002,560 A | 3/1991 | Machold et al. | |
| RE33,569 E | 4/1991 | Gifford, III et al. | |
| 5,007,896 A | 4/1991 | Shiber | |
| 5,007,917 A | 4/1991 | Evans | |
| 5,011,488 A | 4/1991 | Ginsburg | |
| 5,019,088 A | 5/1991 | Farr | |
| 5,041,126 A | 8/1991 | Gianturco | |
| 5,053,008 A | 10/1991 | Bajaj | |
| 5,053,044 A | 10/1991 | Mueller et al. | |
| 5,071,407 A | 12/1991 | Termin et al. | |
| 5,071,425 A | 12/1991 | Gifford, III et al. | |
| 5,085,662 A | 2/1992 | Willard | |
| 5,087,265 A | 2/1992 | Summers | |
| 5,100,423 A | 3/1992 | Fearnot | |
| 5,100,424 A | 3/1992 | Jang et al. | |
| 5,100,425 A | 3/1992 | Fischell et al. | |
| 5,102,415 A | 4/1992 | Guenther et al. | |
| 5,104,399 A | 4/1992 | Lazarus | |
| 5,108,419 A | 4/1992 | Reger et al. | |
| 5,133,733 A | 7/1992 | Rasmussen et al. | |
| 5,135,531 A | 8/1992 | Shiber | |
| 5,152,771 A | 10/1992 | Sabbaghian et al. | |
| 5,152,777 A | 10/1992 | Goldberg et al. | |
| 5,160,342 A | 11/1992 | Reger et al. | |
| 5,171,233 A | 12/1992 | Amplatz et al. | |
| 5,190,546 A | 3/1993 | Jervis | |
| 5,195,955 A | 3/1993 | Don Michael | |
| 5,217,482 A * | 6/1993 | Keith | 606/194 |
| 5,224,953 A | 7/1993 | Morgentaler | |
| 5,306,286 A | 4/1994 | Stack et al. | |
| 5,314,408 A * | 5/1994 | Salmon et al. | 604/22 |
| 5,314,444 A | 5/1994 | Gianturco | |
| 5,314,472 A | 5/1994 | Fontaine | |
| 5,318,576 A | 6/1994 | Plassche, Jr. et al. | |
| 5,329,942 A | 7/1994 | Gunther et al. | |
| 5,330,484 A | 7/1994 | Gunther | |
| 5,330,500 A | 7/1994 | Song | |
| 5,350,398 A | 9/1994 | Pavcnik et al. | |
| 5,354,310 A | 10/1994 | Garnic et al. | |
| 5,356,423 A | 10/1994 | Tihon et al. | |
| 5,366,464 A | 11/1994 | Belknap | |
| 5,366,473 A | 11/1994 | Winston et al. | |
| 5,370,616 A * | 12/1994 | Keith et al. | 604/102.02 |
| 5,370,657 A | 12/1994 | Irie | |
| 5,370,683 A | 12/1994 | Fontaine | |
| 5,376,100 A | 12/1994 | Lefebvre | |
| 5,383,887 A | 1/1995 | Nadal | |
| 5,383,892 A | 1/1995 | Cardon et al. | |
| 5,383,926 A | 1/1995 | Lock et al. | |
| 5,387,235 A | 2/1995 | Chuter | |
| 5,389,087 A * | 2/1995 | Miraki | 604/247 |
| 5,395,349 A | 3/1995 | Quiachon et al. | |
| 5,397,345 A | 3/1995 | Lazerus | |
| 5,405,377 A | 4/1995 | Cragg | |
| 5,409,454 A | 4/1995 | Fischell et al. | |
| 5,415,630 A | 5/1995 | Gory et al. | |
| 5,419,774 A | 5/1995 | Willard et al. | |
| 5,421,832 A | 6/1995 | Lefebvre | |
| 5,423,742 A | 6/1995 | Theron | |
| 5,423,885 A | 6/1995 | Williams | |
| 5,425,765 A | 6/1995 | Tiefenbrun et al. | |
| 5,443,498 A | 8/1995 | Fontaine | |
| 5,449,372 A | 9/1995 | Schmaltz et al. | |
| 4,842,579 A | 10/1995 | Shiber | |
| 5,456,667 A | 10/1995 | Ham et al. | |
| 5,462,529 A | 10/1995 | Simpson et al. | |
| 5,476,104 A | 12/1995 | Sheahon | |
| 5,484,418 A | 1/1996 | Quiachon et al. | |
| 5,507,767 A | 4/1996 | Maeda et al. | |
| 5,512,044 A | 4/1996 | Duer | |
| 5,527,354 A | 6/1996 | Fontaine et al. | |
| 5,536,242 A | 7/1996 | Willard et al. | |
| 5,540,707 A | 7/1996 | Ressemann et al. | |
| 5,549,626 A | 8/1996 | Miller et al. | |
| 5,562,724 A | 10/1996 | Vowerk et al. | |
| 5,569,274 A | 10/1996 | Rapacki et al. | |
| 5,569,275 A | 10/1996 | Kotula et al. | |
| 5,571,094 A * | 11/1996 | Sirhan | 604/284 |
| 5,634,897 A | 6/1997 | Dance et al. | |
| 5,658,296 A | 8/1997 | Bates et al. | |
| 5,662,671 A | 9/1997 | Barbut et al. | |
| 5,669,933 A | 9/1997 | Simon et al. | |
| 5,695,519 A | 12/1997 | Summers et al. | |
| 5,709,704 A | 1/1998 | Nott et al. | |
| 5,720,764 A | 2/1998 | Naderlinger | |
| 5,728,066 A | 3/1998 | Daneshvar | |
| 5,746,758 A | 5/1998 | Nordgren et al. | |
| 5,749,848 A | 5/1998 | Jang et al. | |
| 5,769,816 A | 6/1998 | Barbut et al. | |
| 5,779,716 A | 7/1998 | Cano et al. | |
| 5,792,157 A | 8/1998 | Mische et al. | |
| 5,792,300 A | 8/1998 | Inderbitzen et al. | |
| 5,795,322 A | 8/1998 | Boudewijn | |
| 5,797,952 A | 8/1998 | Klein | |
| 5,800,457 A | 9/1998 | Gelbfish | |
| 5,800,525 A | 9/1998 | Bachinski et al. | |
| 5,807,398 A | 9/1998 | Shaknovich | |
| 5,810,874 A | 9/1998 | Lefebvre | |
| 5,814,064 A | 9/1998 | Daniel et al. | |
| 5,817,102 A | 10/1998 | Johnson et al. | |
| 5,827,324 A | 10/1998 | Cassell et al. | |
| 5,833,644 A | 11/1998 | Zadno-Azizi et al. | |
| 5,833,650 A | 11/1998 | Imran | |
| 5,846,260 A * | 12/1998 | Maahs | 606/200 |
| 5,848,964 A | 12/1998 | Samuels | |
| 5,876,367 A | 3/1999 | Kaganov et al. | |
| 5,893,867 A | 4/1999 | Bagaoisan et al. | |
| 5,895,399 A | 4/1999 | Barbut et al. | |
| 5,902,263 A | 5/1999 | Patterson et al. | |
| 5,906,618 A | 5/1999 | Larson, III | |
| 5,908,435 A | 6/1999 | Samuels | |
| 5,910,154 A | 6/1999 | Tsugita et al. | |
| 5,911,734 A | 6/1999 | Tsugita et al. | |
| 5,916,193 A | 6/1999 | Stevens et al. | |
| 5,925,016 A | 7/1999 | Chornenky et al. | |
| 5,925,060 A | 7/1999 | Forber | |
| 5,925,062 A | 7/1999 | Purdy | |
| 5,925,063 A | 7/1999 | Khosravi | |
| 5,928,203 A | 7/1999 | Davey et al. | |
| 5,928,218 A | 7/1999 | Gelbfish | |
| 5,934,284 A | 8/1999 | Plaia et al. | |
| 5,935,139 A | 8/1999 | Bates | |
| 5,938,645 A | 8/1999 | Gordon | |
| 5,941,869 A | 8/1999 | Patterson et al. | |
| 5,941,896 A | 8/1999 | Kerr | |
| 5,947,995 A | 9/1999 | Samuels | |
| 5,951,585 A | 9/1999 | Cathcart et al. | |
| 5,954,745 A | 9/1999 | Gertler et al. | |
| 5,976,107 A | 11/1999 | Mertens et al. | |
| 5,976,172 A | 11/1999 | Homsma et al. | |
| 5,980,555 A | 11/1999 | Barbut et al. | |
| 5,989,210 A | 11/1999 | Morris et al. | |
| 5,989,271 A | 11/1999 | Bonnette et al. | |
| 5,989,281 A | 11/1999 | Barbut et al. | |
| 5,993,469 A | 11/1999 | McKenzie et al. | |
| 5,997,557 A | 12/1999 | Barbut et al. | |
| 6,001,118 A | 12/1999 | Daniel et al. | |
| 6,007,557 A | 12/1999 | Ambrisco et al. | |

| | | | |
|---|---|---|---|
| 6,010,522 A | 1/2000 | Barbut et al. | |
| 6,013,085 A | 1/2000 | Howard | |
| 6,027,520 A | 2/2000 | Tsugita et al. | |
| 6,042,598 A | 3/2000 | Tsugita et al. | |
| 6,051,014 A | 4/2000 | Jang | |
| 6,051,015 A | 4/2000 | Maahs | |
| 6,053,932 A | 4/2000 | Daniel et al. | |
| 6,059,814 A | 5/2000 | Ladd | |
| 6,066,149 A | 5/2000 | Samson et al. | |
| 6,066,158 A | 5/2000 | Engelson et al. | |
| 6,068,645 A | 5/2000 | Tu | |
| 6,086,605 A | 7/2000 | Barbut et al. | |
| 6,117,154 A | 9/2000 | Barbut et al. | |
| 6,129,739 A | 10/2000 | Khosravi | |
| 6,136,016 A | 10/2000 | Barbut et al. | |
| 6,142,987 A | 11/2000 | Tsugita | |
| 6,152,946 A | 11/2000 | Broome et al. | |
| 6,165,200 A | 12/2000 | Tsugita et al. | |
| 6,168,579 B1 | 1/2001 | Tsugita | |
| 6,171,327 B1 | 1/2001 | Daniel et al. | |
| 6,171,328 B1 | 1/2001 | Addis | |
| 6,179,851 B1 | 1/2001 | Barbut et al. | |
| 6,179,859 B1 | 1/2001 | Bates et al. | |
| 6,179,861 B1 | 1/2001 | Khosravi et al. | |
| 6,203,561 B1 | 3/2001 | Ramee et al. | |
| 6,206,868 B1 | 3/2001 | Parodi | |
| 6,214,026 B1 | 4/2001 | Lepak et al. | |
| 6,221,006 B1 | 4/2001 | Dubrul et al. | |
| 6,224,620 B1 | 5/2001 | Maahs | |
| 6,231,544 B1 | 5/2001 | Tsugita et al. | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,245,087 B1 | 6/2001 | Addis | |
| 6,245,088 B1 | 6/2001 | Lowery | |
| 6,245,089 B1 | 6/2001 | Daniel et al. | |
| 6,258,115 B1 | 7/2001 | Dubrul | |
| 6,264,663 B1 | 7/2001 | Cano | |
| 6,264,672 B1 | 7/2001 | Fisher | |
| 6,270,513 B1 | 8/2001 | Tsugita et al. | |
| 6,277,138 B1 | 8/2001 | Levinson et al. | |
| 6,277,139 B1 | 8/2001 | Levinson et al. | |
| 6,280,413 B1 | 8/2001 | Clark et al. | |
| 6,287,321 B1 | 9/2001 | Jang | |
| 6,290,710 B1 | 9/2001 | Cryer et al. | |
| 6,309,399 B1 | 10/2001 | Barbut et al. | |
| 6,319,268 B1 | 11/2001 | Ambrisco et al. | |
| 6,344,049 B1 | 2/2002 | Levinson et al. | |
| 6,450,975 B1* | 9/2002 | Brennan et al. | 600/585 |
| 6,511,496 B1* | 1/2003 | Huter et al. | 606/200 |
| 6,524,285 B1* | 2/2003 | Sirhan | 604/284 |
| 6,527,746 B1* | 3/2003 | Oslund et al. | 604/160 |
| 6,616,679 B1 | 9/2003 | Khosravi et al. | |
| 6,616,681 B2 | 9/2003 | Hanson et al. | |
| 6,685,722 B1 | 2/2004 | Rosenbluth et al. | |
| 6,743,246 B1* | 6/2004 | Maahs | 606/200 |
| 6,793,648 B2* | 9/2004 | Oslund et al. | 604/160 |
| 6,824,554 B1* | 11/2004 | Jang | 606/194 |
| 7,208,001 B2* | 4/2007 | Coyle et al. | 606/194 |
| 2002/0004667 A1* | 1/2002 | Adams et al. | 606/200 |
| 2002/0072712 A1* | 6/2002 | Nool et al. | 604/167.01 |
| 2002/0082525 A1 | 6/2002 | Oslund et al. | |
| 2002/0095141 A1 | 7/2002 | Belef et al. | |
| 2002/0151927 A1* | 10/2002 | Douk et al. | 606/200 |
| 2003/0233117 A1* | 12/2003 | Adams et al. | 606/200 |
| 2004/0044359 A1* | 3/2004 | Renati et al. | 606/200 |
| 2004/0225259 A1* | 11/2004 | Oslund et al. | 604/160 |
| 2004/0254602 A1* | 12/2004 | Lehe et al. | 606/200 |
| 2004/0260333 A1 | 12/2004 | Dubrul et al. | |
| 2005/0113688 A1* | 5/2005 | Nita et al. | 600/437 |

FOREIGN PATENT DOCUMENTS

| | | |
|---|---|---|
| DE | 34 17 738 | 11/1985 |
| DE | 40 30 998 A1 | 10/1990 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| FR | 2 580 504 | 10/1986 |
| FR | 2 643 250 A1 | 8/1990 |
| FR | 2 666 980 | 3/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | 94/11038 A1 | 5/1994 |
| WO | WO 94/14389 | 7/1994 |
| WO | WO 94/24946 | 11/1994 |
| WO | WO 96/01591 | 1/1996 |
| WO | WO 96/04875 A1 | 2/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | 00/69500 A1 | 11/2000 |
| WO | WO 00/69499 | 11/2000 |
| WO | WO 00/76390 | 12/2000 |
| WO | WO/01/08743 | 2/2001 |
| WO | WO 01/67989 | 9/2001 |
| WO | WO 02/054988 | 7/2002 |
| WO | WO 03/002033 | 1/2003 |
| WO | WO 03/034941 | 5/2003 |

OTHER PUBLICATIONS

"Endovascular Grafts, Stents Drive Interventional Radiology Growth," *Cardiovascular Device Update*, 2(3):1-12 (Mar. 1996).
"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40. (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," *Catheterization and Cardiovascular Diagnosis*, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic arch of patients with systemic embolization: A new finding seen by transesophageal echocardiography," *American Heart Journal* 120(3):658-660 (Sep. 1990).

Waksman et al., "Distal Embolization is Common After Directional Atherectomy . . . ," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

* cited by examiner

SHEATH FOR USE WITH AN EMBOLIC PROTECTION FILTER

FIELD OF THE INVENTION

The present invention pertains to embolic protection filter devices. More particularly, the present invention pertains to filtering devices with a sheath and methods for making and using filtering devices with a sheath.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences because the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature. During angioplasty procedures, stenotic debris may also break loose due to manipulation of the blood vessel. Because of this debris, a number of devices, termed embolic protection devices, have been developed to filter out this debris. There is an ongoing need to provide alternative filtering devices as well as methods for making and using filtering devices.

BRIEF SUMMARY

The invention provides design, material, and manufacturing method alternatives for embolic protection filtering devices. Exemplary filtering devices include an elongate shaft or filter wire, a filter coupled to the filter wire, and a sheath. The methods for using the filtering device include using an introducer member to help back load a guidewire into the sheath and then advance the filtering device along the guidewire to a target region. Once positioned, for example, the guidewire can be removed and the filtering device may be used for its intended purpose.

The above summary of some embodiments is not intended to describe each disclosed embodiment or every implementation of the present invention. The Figures, and Detailed Description, which follow, more particularly exemplify these embodiments.

DETAILED DESCRIPTION

The following description should be read with reference to the drawings wherein like reference numerals indicate like elements throughout the several views. The detailed description and drawings illustrate example embodiments of the claimed invention.

When a clinician performs an intravascular intervention such as angioplasty, atherectomy, and the like, embolic debris may dislodge from the blood vessel that can travel in the bloodstream to a position where it may impair blood flow, possibly leading to tissue damage. A number of other situations and/or interventions may also result in the mobilization of embolic debris. Accordingly, embolic protection filtering devices have been developed that can be disposed in the blood vessel downstream of the treatment site and expanded to capture debris.

Figure 1:
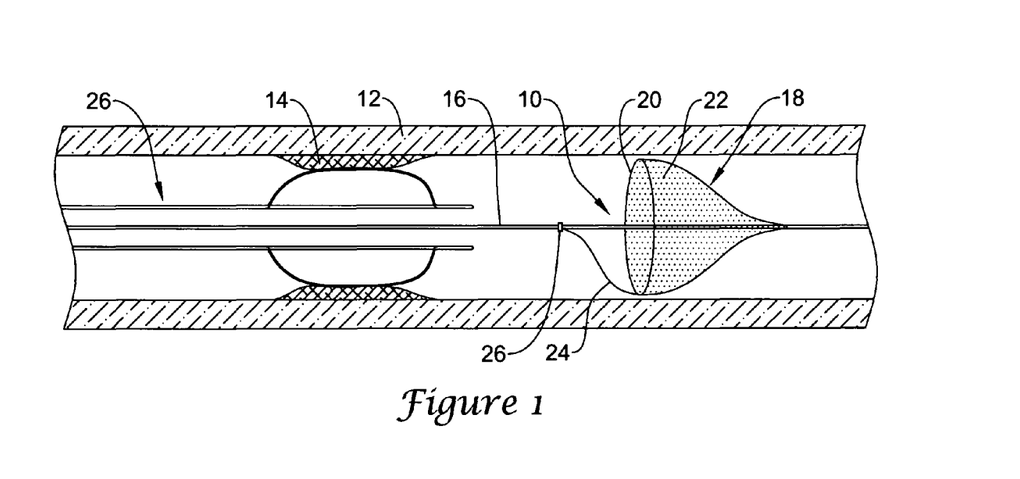
FIG. 1 is a partial cross-sectional plan view of an example filtering device disposed in a blood vessel.

FIG. 1 is a partial cross-sectional view of an example embolic protection filtering device 10 disposed within a blood vessel 12 adjacent an intravascular lesion 14. Device 10 may include an elongate shaft or filter wire 16 having an embolic protection filter 18 coupled thereto. Filter 18 may include a filter frame 20 and a filter material or fabric 22 coupled to filter frame 20. In general, filter 18 may be adapted to operate between a first generally collapsed configuration and a second generally expanded configuration for collecting debris in a body lumen. Frame 20 may be comprised of a "self-expanding" shape-memory material such as nickel-titanium alloy, which is capable of biasing filter 18 toward being in the second expanded configuration. Additionally, frame 20 may include a radiopaque material or include, for example, a radiopaque wire disposed about a portion thereof. Some further details regarding these and other suitable materials is provided below. Filter material 22 can be drilled (for example, formed by known laser techniques) or otherwise manufactured to include at least one opening. The holes or openings can be sized to allow blood flow therethrough but restrict flow of debris or emboli floating in the body lumen or cavity. One or more struts 24 may extend between frame 20 and filter wire 16 and be coupled to filter wire 16 by a coupling 26. Coupling 26 may be one or more windings of struts 24 about filter wire 16 or be a fitting disposed over an end of struts 24 to attach it to filter wire 16.

Filter wire 16 (or any other appropriate structure described herein such as filter frame 20) may include any suitable materials such as a metal, metal alloy, polymer, metal-polymer composite, and the like, or any other suitable material. Some examples of suitable metals and metal alloys include stainless steel, such as 304V, 304L, and 316LV stainless steel; mild steel; nickel-titanium alloy such as linear-elastic or superelastic nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; other Co—Cr alloys; platinum enriched stainless steel; or other suitable material.

As mentioned above, filtering device 10 or portions thereof, may also be doped with or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, molybdenum, palladium, tantalum, tungsten or tungsten alloy, plastic material loaded with a radiopaque filler, and the like.

With filter 18 properly positioned in blood vessel 12, another medical device 26 may be advanced over filter wire 16 in order to treat and/or diagnose lesion 14. For example, a catheter 26 (such as the balloon catheter depicted in FIG. 1) may be advanced over filter wire 16 in order to expand lesion 14. Of course numerous other devices could just as easily be passed over filter wire 16 including any device designed to pass through an opening or body lumen. For example, the device may comprise any type of catheter (e.g., therapeutic, diagnostic, or guide catheter), a stent delivery catheter, an endoscopic device, a laproscopic device, and the like, or any other suitable device.

Figure 2:
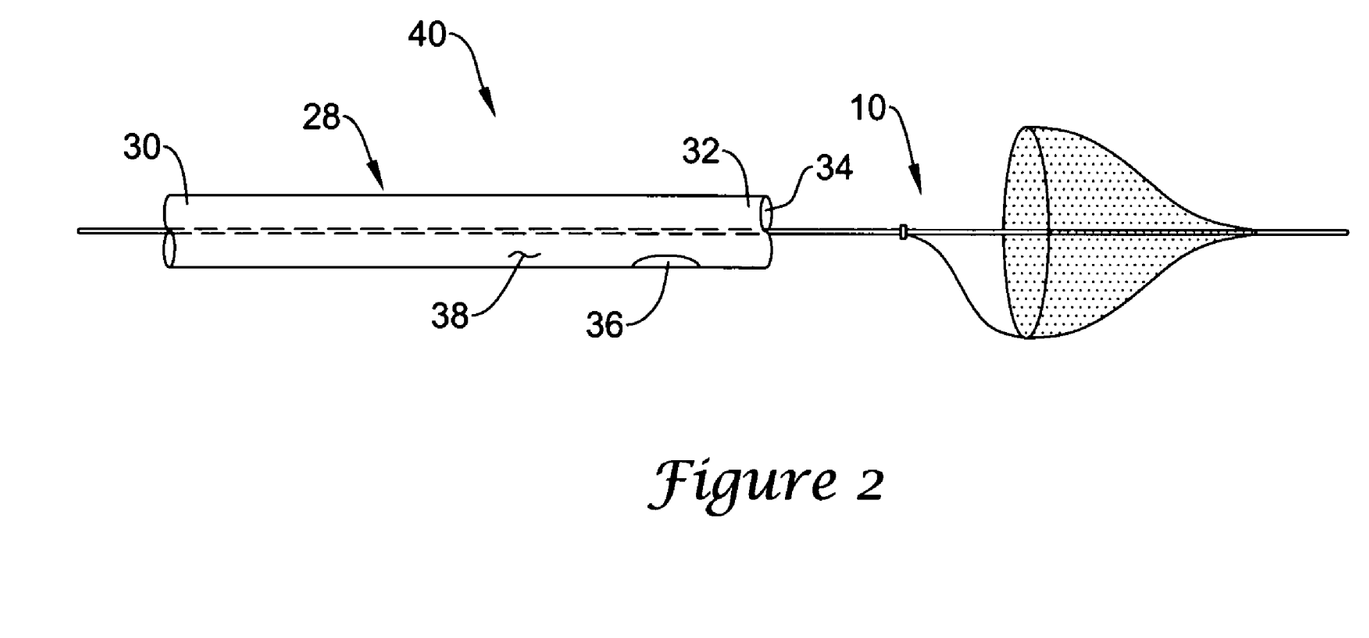
FIG. 2 is a side view of an example filtering device.

FIG. 2 depicts filtering device 10 along with a sheath 28. Sheath 28 comprises a generally tubular elongate structure having a proximal end region 30, a distal end region 32, and a lumen 34 extending at least partially the length therethrough. A port or opening 36 may be defined in sheath 28, which provide access to lumen 34 from the exterior surface 38 of sheath 28. For convenience, sheath 28 and filtering device 10, collectively, are referred to subsequently as the "filtering apparatus" and denoted with reference number 40.

Sheath 28 may be made from any suitable material including polymers or any other material described herein. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM. Engineering Plastics), ether or ester based copolymers (for example, butylene/poly (alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like. In some embodiments sheath 26 can be blended with a liquid crystal polymer (LCP). For example, the mixture can contain up to about 6% LCP.

In some embodiments, sheath 26 may include a self-sealing material, for example, near port 36 such as a polymer, rubber, a rubber septum, and the like, or any other suitable material. By utilizing a rubber septum near port 36, object can pass through port 36 and, upon removal of the object, port 36 will self-seal. The phrase self-seal in relation to port 36 is understood to mean that the seal formed around port 36 remain substantially resistant to the passage of air or fluids after an object is removed from a rubber septum. Alternatively, a rubber septum or other suitable seal can be disposed at port 36 to achieve the same result. In addition to the sealing characteristics described above, this structural feature may also help add column strength adjacent port 36.

In at least some embodiments, filtering apparatus 40 has a number of desirable design characteristics. For example, by including port 36, apparatus 40 may be used in conjunction with essentially any available guidewire or guiding structure including typical 0.014 inch diameter guidewires and the like. This feature is desirable given that many physicians tend to have a preference for a particular, commercially available guidewire. Thus, if another device is intended to be used with the guidewire, it must be "compatible" or usable with the guidewire. Apparatus 40 fits this need by being designed to have wide ranging compatibility with numerous devices. Therefore, physicians do not need to give up their preferred guidewire in order to take advantage of the diagnostic and therapeutic benefits of apparatus 40. Furthermore, by including port 36 instead of merely providing a separate guidewire lumen, the profile of apparatus 40 can be kept compact so that apparatus 40 can access deep vascular locations in an atraumatic manner. This may allow apparatus 40 to gain access to particularly small and/or sensitive regions of the anatomy such as the central nervous system.

Figure 3:
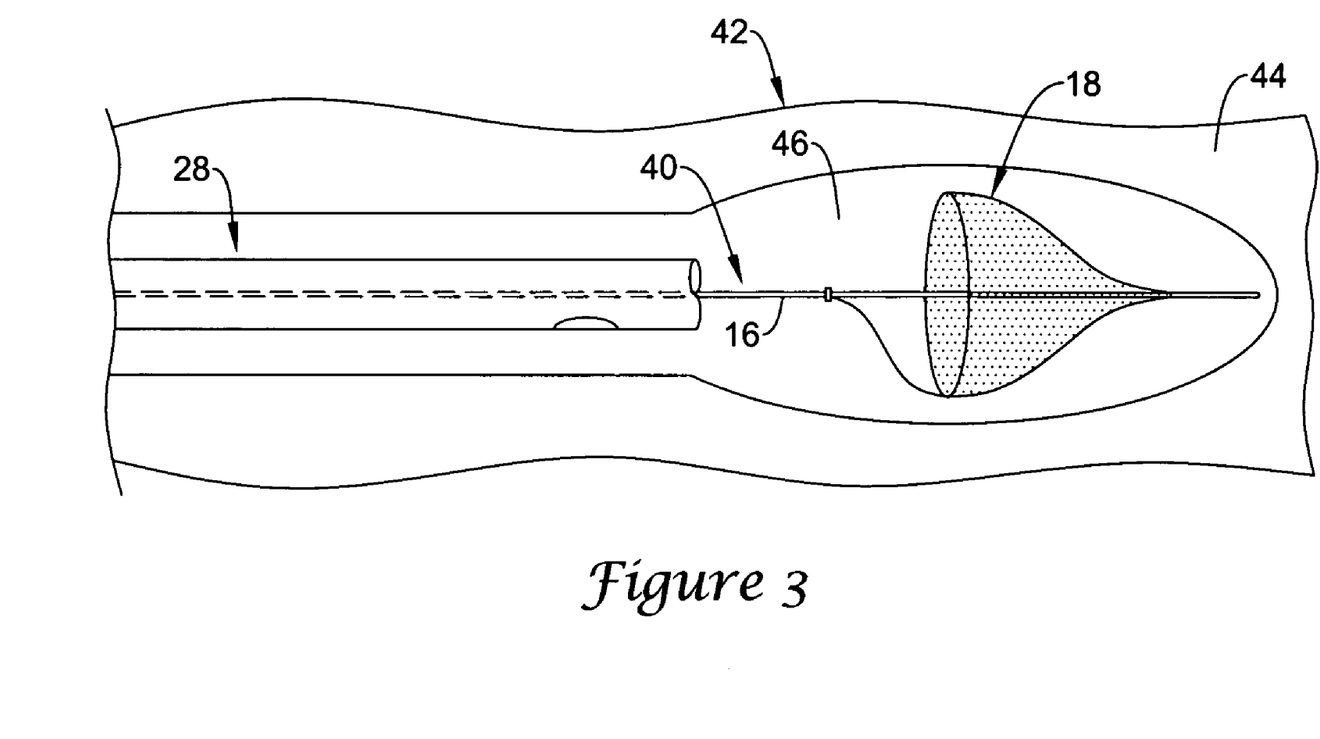
FIG. 3 is a cutaway view of an example filtering device in suitable consumer packaging.

FIG. 3 depicts a package or kit 42 that an end user (i.e., physician or other clinician) might expect to see. Kit 42 may include a generally planar backing 44 that includes one or more depressions 46 formed therein that are designed to accommodate filter 18 and sheath. A covering (not shown) may be disposed over backing and apparatus 40 so as to maintain the sterility of apparatus 40. Numerous variations are contemplated for kit 42 according to the general practice and procedure for medical device packaging.

It can also be seen in FIG. 3 that kit 42 allows filter 18 to be packaged outside of sheath 28. This may desirably help filter 18 retain its expanded shape and help sheath 28 from being deformed or "stretched" by virtue of filter 18 being disposed therein for an extending period of time. Prior to use, a clinician needs only to open kit 42 and back load filter 18 into sheath 26. Back loading, a term that is used throughout this description, is understood to be a process in which an object is retracted or otherwise pulled into or through another object. For example, back loading filter 18 can occur by pulling filter wire 16 proximally so that filter 18 backs into distal end region 32 of sheath 26.

Figure 4:
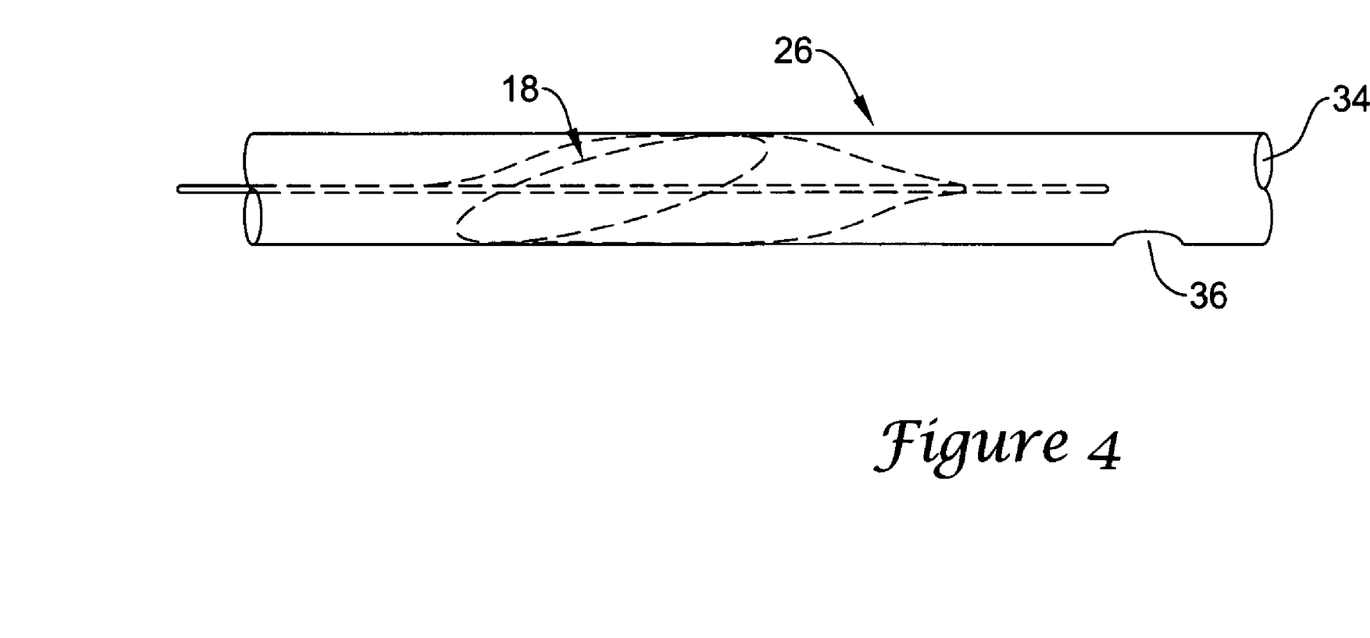
FIG. 4 is a side view of an example filtering device where the filter is collapsed within a sheath.

The result of back loading filter 18 into sheath 26 is depicted in FIG. 4. Here it can be seen that filter 18 (shown in phantom) is collapsed and disposed within lumen 34 of sheath 26. In at least some embodiments, it may be desirable to back load filter 18 to a position that is proximal of port 36.

This feature allows a guidewire 48 (not shown in FIG. 4, best seen in FIG. 5) to be more easily back loaded into sheath 26 and, ultimately, through port 36 without interference from filter 18.

Figure 5:
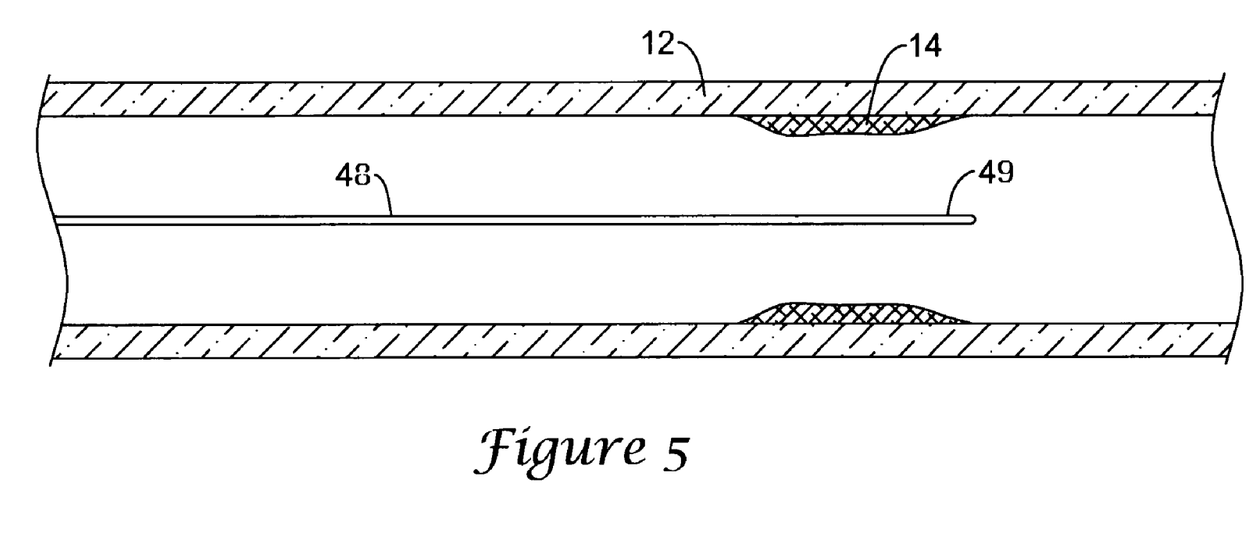
FIG. 5 is partial cross-sectional plan view depicting a guidewire disposed in a blood vessel adjacent a target region.

With filter 18 properly back loaded into sheath 26, apparatus 40 can be advanced over guidewire 48. Guidewire 48, as suggested above, may be the clinician's preferred guidewire and can be advanced through blood vessel 12 to a position adjacent lesion 14 as seen in FIG. 5. The proper positioning of guidewire 48 may include disposing a distal end 49 of guidewire 48 beyond or otherwise adjacent lesion 14 while a proximal end 50 (not shown in FIG. 5, best seen in FIG. 7) of guidewire 48 remains outside the body of the patient. In some embodiments, distal end 32 of sheath 26 may be tapered, strengthened, made more elastic, or otherwise configured to improve the ability of sheath 26 to cross lesion 14.

Figure 6:
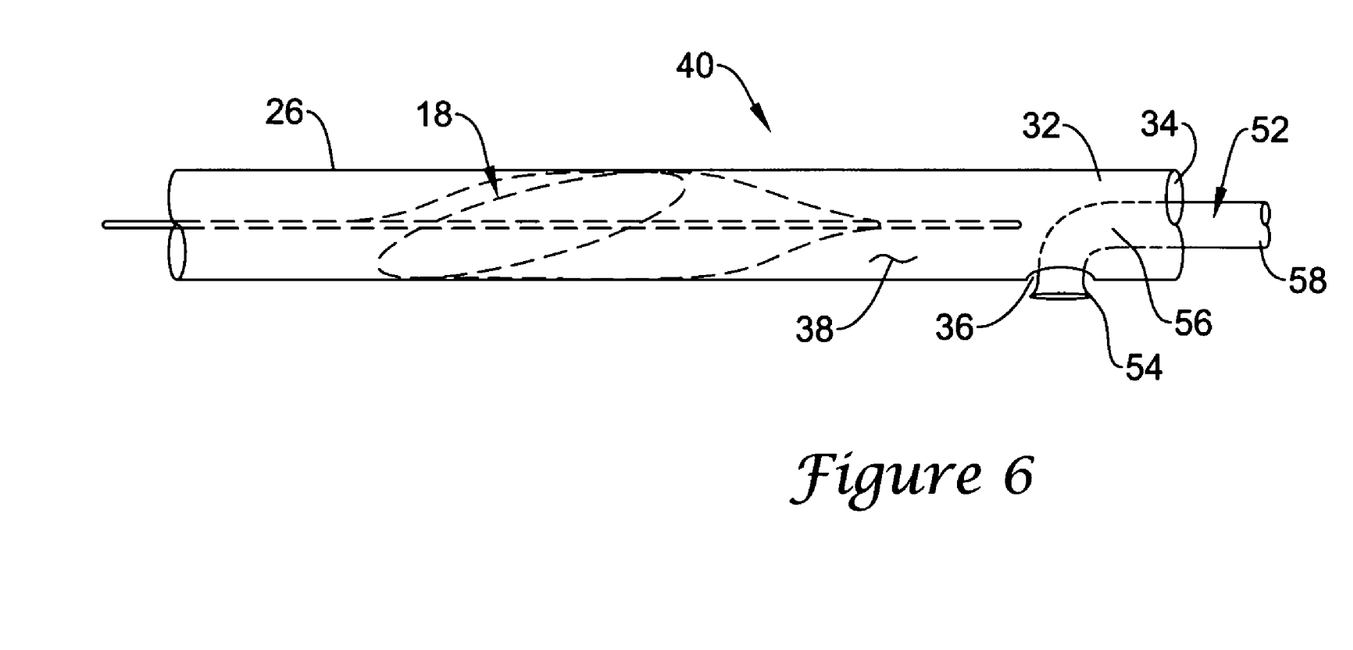
FIG. 6 is a side view of an example filtering device having an introducer member coupled thereto.

Proximal end 50 of guidewire 48 can be back loaded into sheath 26 by pulling proximal end 50 into lumen 34 and through port 36 so that proximal end 50 is generally disposed along exterior surface 38 of sheath 26. In order to improve the ability of the clinician to back load guidewire 48 into sheath 26, an introducer member 52 may be inserted through port 36 as shown in FIG. 6. According to this embodiment, introducer member 52 may have a first end 54 disposed along exterior surface 38, a body portion 56 extending through port 36 and into lumen 34, and a second end 58 positioned distally of distal end 32 of sheath 26. For example, second end 58 may extend about 2 to about 10 millimeters distally beyond distal end 32. In some embodiments, first end 54 has a flared or trumpet-like shape. This shape may, for example, facilitate insertion and removal of introducer member 52 from port 36. Introducer member 52 may be made from any suitable material including any of those materials described herein. It should be noted that introducer member 52 could be placed in port 36 prior to packaging so that introducer member 52 is included with kit 42.

Figure 7:
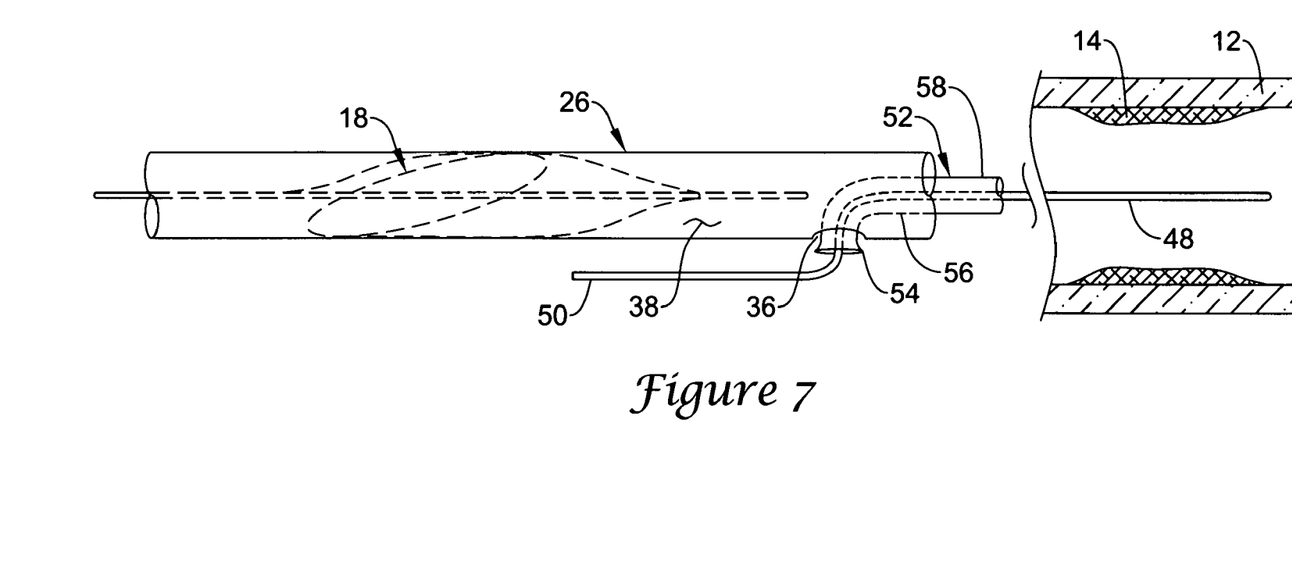
FIG. 7 is a partial cross-section side view depicting the guidewire of FIG. 5 being back loaded through the introducer member.
Figure 8:
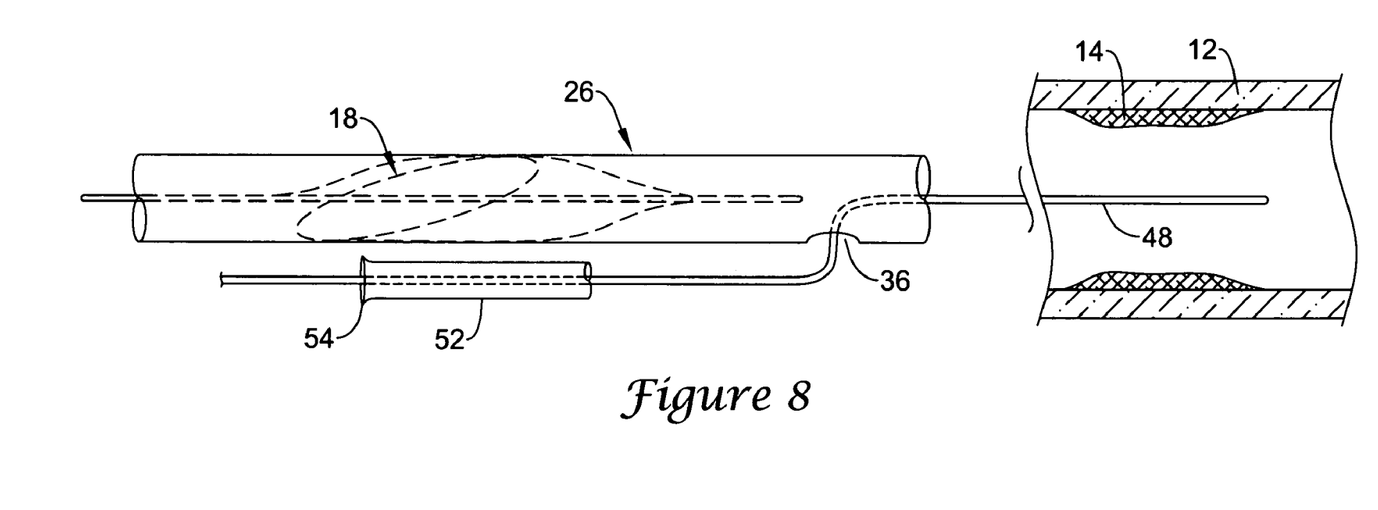
FIG. 8 is a partial cross-section side view depicting the introducer member being removed from the filtering device.
Figure 9:
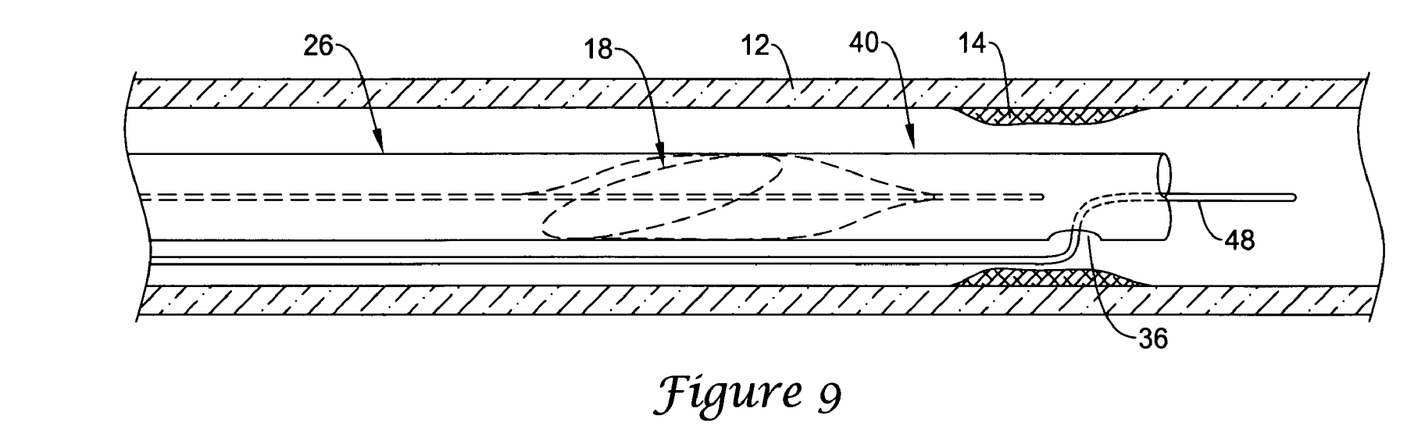
FIG. 9 is a partial cross-section side view depicting the filtering device being advanced over the guidewire.

Proximal end 50 of guidewire 48 can be back loaded by extending it through second end 58, through body portion 56, and out of first end 54 so to a position along exterior surface 38 of sheath as shown in FIG. 7. Once guidewire 48 is back loaded and proximal end 50 is accessible along exterior surface 38, introducer member 52 may be removed from port 36 as depicted in FIG. 8. Removal of introducer member 52 may include grasping first end 54 and pulling introducer member 52 from port 36.

Figure 10:
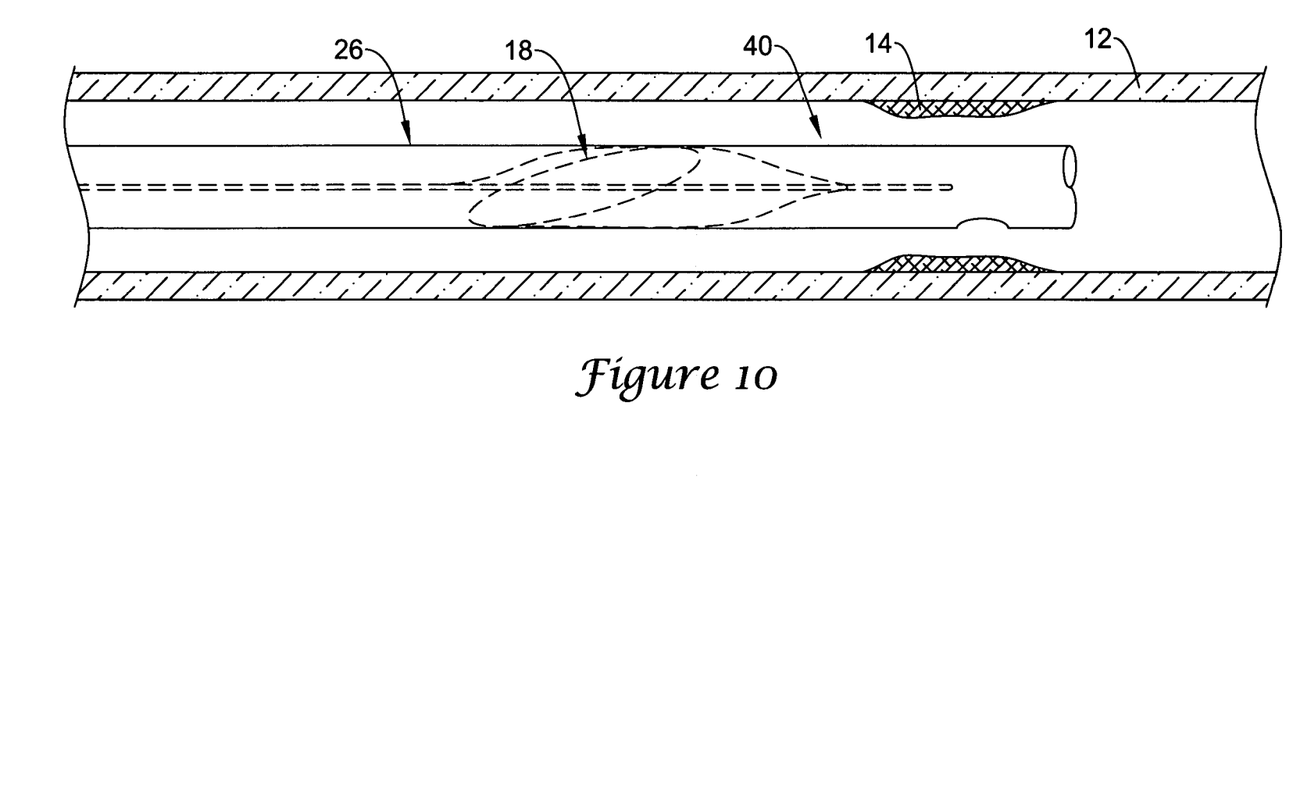
FIG. 10 is a partial cross-sectional side view where the guidewire is removed.
Figure 11:
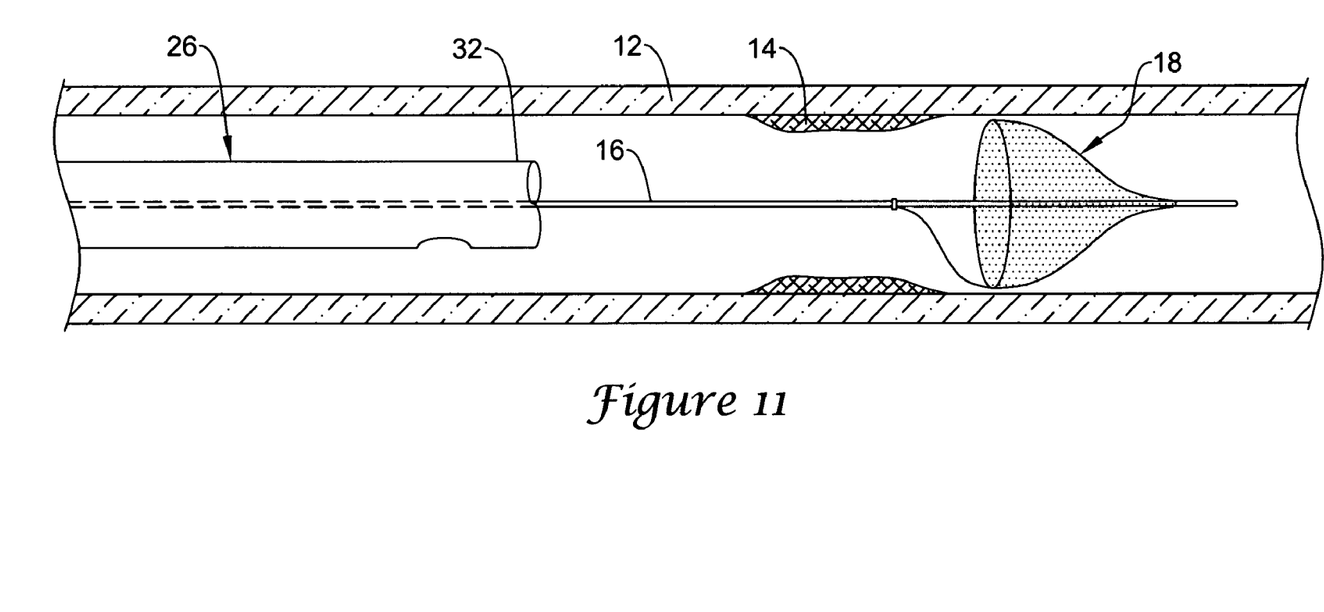
FIG. 11 is a partial cross-sectional side view depicting the filter expanded in the blood vessel.

With guidewire 48 extending through port 36, apparatus 40 can be advanced over guidewire 48 to a suitable position adjacent lesion 14, for example, across or "downstream" of lesion 14. With apparatus 40 properly positioned, guidewire 48 can be removed by proximally retracting it as depicted in FIG. 10. For example, the clinician may simply grasp proximal end 50 (which is accessible outside the patient's body) and pull guidewire 48 out from vessel 12. Finally, sheath 26 can be proximally retracted to allow filter 18 to be delivered or otherwise emerge from distal end 32 so as to expand and generally conform to blood vessel 12 as seen in FIG. 11. With filter 18 deployed, another medical device may be advanced over filter wire 16 as shown in FIG. 1 so that the desired diagnostic or therapeutic procedure may be performed. Upon completion of the intervention, filtering device 10 can be retrieved from the vasculature using a typical retrieval sheath. In some embodiments, the retrieval sheath is the same or similar to sheath 26.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method for using an embolic protection filter assembly, comprising the steps of:
   providing an embolic protection filter assembly, the assembly including an elongate shaft, a filter coupled to the shaft, and a sheath disposed about a portion of the shaft and positioned adjacent the filter, the sheath including a port through a side wall of the sheath;
   shifting the filter to a first position within the sheath, wherein the first position includes at least a portion of the filter being positioned proximally of the port and collapsed within the sheath;
   providing a guidewire having a proximal end and a distal end;
   advancing the guidewire through a blood vessel so that the distal end is positioned adjacent a target region;
   inserting a removable introducer member through the port, the introducer member having a first end, a body portion, and a second end;
   configuring the introducer member so that the first end is disposed along an exterior surface of the sheath, the body portion extends through the port and into a lumen defined by the sheath, and the second end is disposed distally of a distal end of the sheath;
   passing the proximal end of the guidewire through the introducer member and the sheath simultaneously;
   advancing the filter assembly over the guidewire until the filter assembly is positioned adjacent the target region;
   retracting the guidewire from the blood vessel; and
   shifting the filter to a second position, wherein the second position includes the filter being positioned distally of the sheath and expanded.

2. The method of claim 1, wherein the step of shifting the filter to a first position within the sheath includes proximally retracting the filter within the sheath.

3. The method of claim 1, wherein the first end portion is flared.

4. The method of claim 1, wherein the step of advancing the filter assembly over the guidewire until the filter assembly is positioned adjacent the target region includes passing the guidewire through the body portion of the introducer member.

5. The method of claim 4, wherein the step of passing the guidewire through the body portion of the introducer member includes passing the guidewire through the first end portion.

6. The method of claim 1, wherein the step of retracting the guidewire from the blood vessel through the introducer includes completely removing the guidewire from the vessel and the introducer.

7. The method of claim 1, wherein the step of shifting the filter to a second position includes distally advancing the elongate shaft.

8. The method of claim 1, further comprising the step of removing the introducer member from the sheath.

9. The method of claim 8, wherein the step of removing the introducer member from the sheath occurs before the step of advancing the filter assembly over the guidewire until the filter assembly is positioned adjacent the target region.

10. The method of claim 1, further comprising the step of removing the sheath from the blood vessel.

11. The method of claim 1, further comprising the step of advancing a catheter over the elongate shaft to a position adjacent the target region and the filter.

12. The method of claim 11, wherein catheter includes a balloon catheter.

13. The method of claim 11, wherein the catheter includes a stent delivery catheter.

14. A method for using an embolic protection filter assembly, comprising the steps of:

provcing an embolic protection filter assembly, the assembly including a filter wire, a filter coupled to the filter wire, and a sheath having a side port defined therein and having a lumen;

disposing the filter within the lumen of the sheath at a position proximal of the port;

providing an introducer member, the introducer having a first end, a body portion, and a second end;

configuring the introducer member so that the first end is disposed along an exterior surface of the sheath, the body portion extends through the port and into the lumen, and the second end is disposed distally of a distal end of the sheath;

providing a guidewire having a proximal end and a distal end;

advancing the guidewire through a blood vessel so that the distal end is positioned adjacent a target region;

back loading the proximal end of the guidewire into the introducer member;

removing the introducer member from the sheath;

advancing the filter assembly over the guidewire to a position adjacent the target region;

retracting the guidewire from the blood vessel; and advancing the filter out from the distal end of the sheath so that the filter expands within the blood vessel.

15. The method of claim 14, wherein the step of disposing the filter within the lumen of the sheath at a position proximal of the port includes back-loading the filter into the sheath.

16. The method of claim 14, wherein the first end of the introducer member is flared.

17. The method of claim 14, further comprising the step of removing the sheath from the blood vessel.

18. The method of claim 14, further comprising the step of advancing a catheter over the filter wire to a position adjacent the target region and the filter.

19. The method of claim 18, wherein the catheter includes a balloon catheter.

20. The method of claim 18, wherein the catheter includes a stent delivery catheter.

21. An embolic protection filter assembly, comprising:

a tubular sheath having a proximal end, a distal end, a lumen defined therein, and a port positioned proximally of the distal end;

an elongate filter wire;

a filter attached to the filter wire;

wherein at least a portion of the filter wire is disposed within the lumen;

an introducer member removably attached to the sheath adjacent the port, the introducer member having a first end, a body portion, and a second end; and wherein the first end is disposed along an exterior surface of the sheath, the body portion extends through the port and into the lumen, and the second end is positioned distally of the distal end of the sheath.

22. The assembly of claim 21, wherein the first end of the introducer member is flared.

\* \* \* \* \*